United States Patent [19]

Chatterji et al.

[11] 4,405,611

[45] Sep. 20, 1983

[54] BISULFITE STABILIZATION OF 5-AZACYTIDINE

[75] Inventors: Dulal C. Chatterji, Germantown; Joseph F. Gallelli, Bethesda, both of Md.

[73] Assignee: The United States of America as represented by the Department of Health and Human Services, Washington, D.C.

[21] Appl. No.: 331,989

[22] Filed: Dec. 18, 1981

Related U.S. Application Data

[63] Continuation-in-part of Ser. No. 163,521, Jun. 27, 1980, abandoned.

[51] Int. Cl.³ .............................................. A61K 31/70
[52] U.S. Cl. ....................................... 424/180; 536/23
[58] Field of Search ........................... 424/180; 536/23

[56] References Cited

U.S. PATENT DOCUMENTS 4,058,602 11/1977 Beisler et al. .......................... 536/23

OTHER PUBLICATIONS

Chatteyi et al., Journal of Pharmaceutical Sciences, vol. 68, pp. 822–826, 1979.
Notari et al., J. Pharm. Science, vol. 64, pp. 1148–1157, 1975.

*Primary Examiner*—Blondel Hazel
*Attorney, Agent, or Firm*—John S. Roberts, Jr.

[57] ABSTRACT

A bisulfite addition product of 5-azacytidine and method wherein bisulfite is added to the azacytidine molecule at the 5-6 protonated imine bond. It is significant and advantageous to maintain the compound in this pro-drug form. At a pH above 6 and including higher physiological pH in animals, the bisulfite form reverts to the parent compound, rendering it readily available for utilization in the body. This product is produced as the bisulfite addition product at preferably a pH of 2.5.

2 Claims, 3 Drawing Figures

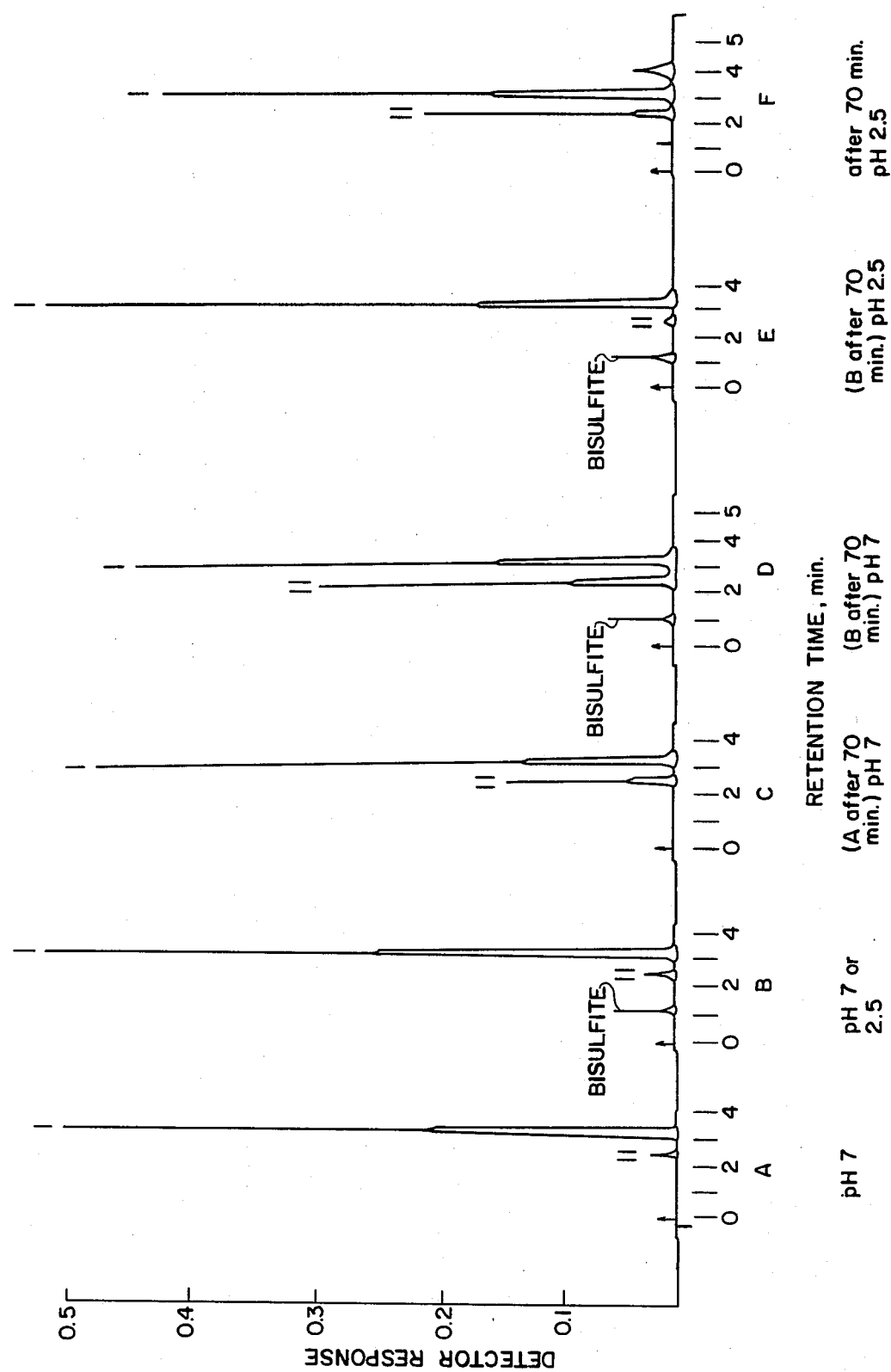

BISULFITE STABILIZATION OF 5-AZACYTIDINE

This application is a continuation-in-part application of pending Ser. No. 163,521 filed June 27, 1980 now abandoned.

BACKGROUND

The drug 5-azacytidine is currently being evaluated against a resistant form of leukemia. Due to the side effects of nausea and vomiting, which limit the dose, it is a preferred method of treatment to infuse the drug slowly. However, the instability of the drug and thereby its subsequent loss is a serious drawback to the infusion.

Even when the drug is infused in lactated Ringer injection technique, which provides optimum stability conditions for the drug at pH 6.4, about 10% of the drug is lost in 2 hours at room temperature.

What is required is a means to stabilize the drug. The creation of a pro-drug form has several requirements. The stability in the pro-drug form must last the requisite infusion time. Secondly, the pro-drug form must be free of toxicity. Thirdly, the active drug form must be released under physiological conditions.

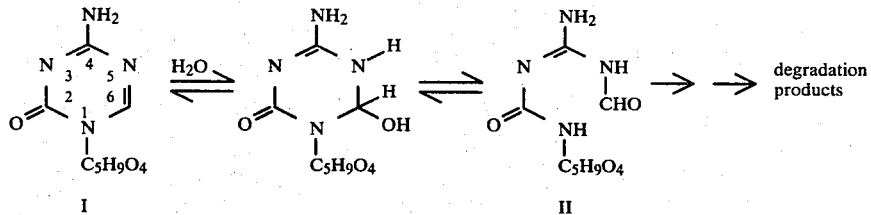

The present invention presents a means to meet these requirements in a safe and acceptable manner.

STATEMENT OF PRIOR ART

Notari and DeYoung have investigated the kinetics of mechanism of 5-azacytidine degradation (Robert E. Notari and Joyce L. DeYoung, "Kinetics and Mechanisms of Degradation of the Antileukemic Agent 5-Azacytidine in Aqueous Solutions," *Journal of Pharmaceutical Science*, 64 (1975), pp. 1148–1157). Absorbance studies with varying bisulfite concentrations on 5-azacytidine were done and it was suggested that a possible addition analogous to addition with 5-azacytosine may account for the lessening intensity of the absorbance. No pH or pro-drug investigations with bisulfite and 5-azacytidine were pursued.

STATEMENT OF UTILITY

The 5-azacytidine forms a pro-drug by nucleophilic addition of bisulfite ion. This pro-drug has been shown in animals to revert to the active compound at a pH of about 6 and to give back the parent compound, thus performing a unique use for a compound which presently is being used against a resistant form of leukemia.

SUMMARY OF THE INVENTION

The 5-azacytidine is stabilized by nucleophilic addition of bisulfite ion and thus counteracts a degradation tendency of the drug, which had heretofore presented serious difficulties in animals. 5-Azacytidine stability in bisulfite here was increased approximately ten-fold over its stability in water or lactated Ringer injection by the addition of excess sodium bisulfite and the maintenance of a pH of about 2.5. The increased stability in the presence of bisulfite at pH of 2.5 is attributed to the addition of bisulfite across the 5–6 imine bond which prevented the hydrolytic attack on this labile double bond. However, above pH 4, bisulfite increased degradation. At higher pH the compound was not longer protonated and bisulfite did not form the stable addition compound. The addition compound quickly decomposed above pH 6 to give back the parent compound and thus acts as a pro-drug. Thus, when the pro-drug enters the animal body, the physiological sites, which all have a pH greater than 6, present an environment into which the pro-drug is instantly converted to the drug.

The intact drug remaining was assayed by high pressure liquid chromatography (HPLC) and the reversability of the bisulfite addition product above pH 6 was demonstrated by u.v. spectrophotometry and HPLC. It is well known the bisulfite does not present any toxicity threat to the human body.

In the following schemat the hydrolysis of 5-azacytidine, designated I, is shown. It is a classical acid catalyzed hydration of the 5-6 imine double bond followed by deamination to yield of derivative, N-(formylamidino)-N-beta-D-ribofuranosylurea, designated II.

The use of 5-azacytidine (I) in acute myelogenous leukemia is often limited by severe and sometimes dose-limiting nausea and vomiting. Although the GI toxicity can be controlled effectively by administering the drug as a slow infusion, extreme drug instability poses a serious problem. Even when I is infused in lactated Ringer injection, which provides optimum stability conditions for the drug at pH 6.4, about 10% of I is lost in 2 hours at room temperature.

STABILIZING THE DOUBLE BOND

An effective approach to render the 5–6 double bond of I stable to water attack is to add a stronger nucleophile capable of attacking the 5–6 double bond preferentially over water. Such a nucleophile would assure that the addition product does not undergo subsequent deamination; it would be stable in the infusion solution and, most important, it would quickly convert back to I under physiological conditions. The nucleophile would also be physiologically compatible.

Sodium bisulfite is a strong nucleophile and a common antioxidant additive in various pharmaceutical preparations.

FIG. 1 is a graph of chromatograms obtained by high pressure liquid chromatography (HPLC) of various solutions of I with or without bisulfite.

Figure 3:
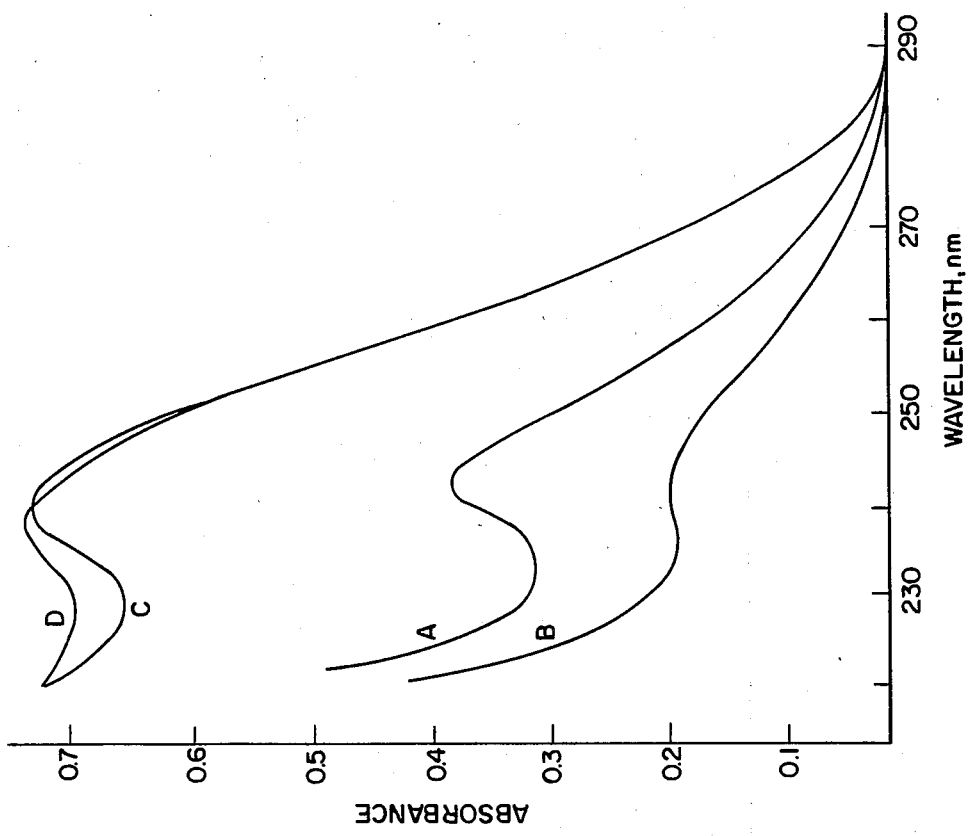
FIG. 3 is a u.v. spectrum of I and I with bisulfite.

Standard HPLC procedures with a mobile phase of a pH of 6.5 established the chromatograms for I in various states. FIG. 1A shows I, freshly prepared at a pH of 7; FIG. 1B shows I with bisulfite, freshly prepared at a pH of 2.5 or 7; FIG. 1C shows A after 70 minutes; FIG. 1D shows B at pH 7 after 70 minutes; FIG. 1E shows B at pH 2.5 after 70 minutes and FIG. 1F shows I alone after 70 minutes at pH 7. This shows that bisulfite has a strong stabilizing effect of I hydrolyses at pH 2.5 (compare FIGS. 1C–1E).

The effect of bisulfite on the stability of I at various pH levels is given in Table 1 below.

TABLE 1

Time for I to Reach 90% of Its Original Concentration (0.5 mg/ml) in Buffer Solutions at Room Temperature (23-26°)

| | | Time to Reach 90%, hr | |
|---|---|---|---|
| pH | Buffer | With Bisulfite[a] | Without Bisulfite |
| 6.3 | Lactated Ringer injection | — | 2.3 |
| 7.0 | 0.05 M phosphate | 0.8 | 2.6 |
| 6.5 | 0.05 M phosphate | 1.2 | 2.3 |
| 6.0 | 0.05 M phosphate | 1.0 | 1.5 |
| 4.0 | 0.05 M acetate | 1.3 | 1.4 |
| 3.2 | 0.05 M phosphate | 8.7 | 1.2 |
| 2.5 | 0.05 M phosphate | 20 | 1.1 |
| 2.5 | 0.05 M phosphate | 18[b] | — |
| 2.5 | 0.05 M phosphate | 6[c] | — |
| 2.5 | 0.05 M phosphate | 96[d] | — |

[a]Sodium bisulfite, 5 mg/ml, unless specified otherwise.
[b]Sodium bisulfite, 3 mg/ml.
[c]Sodium bisulfite, 1 mg/ml.
[d]Refrigeration temperature (2-6°).

Table 1 shows the conventional lactated Ringer injection for comparison purposes. (Ringer injection is a sterile solution of calcium chloride, potassium chloride, sodium chloride, and sodium lactate in water for injection.) Comparisons above the double line, that is, a pH value greater than 4.0, indicate that the effect of the bisulfite increased the I degradation rate.

However, below pH 4.0, bisulfite slowed I degradation; the stabilization was more pronounced as the solution pH approached 2.5. Furthermore, at pH 2.5, increasing the amount of bisulfite increased the stabilization. At pH 2.5 in the presence of a 10-fold excess of bisulfite (5 mg of sodium bisulfite/ml with 0.5 mg of I/ml), about 20 hours was required for 10% degradation at room temperature. This represents almost one order of magnitude improvement over the stability of I in the presently used clinical formulation of drug in lactated Ringer injection.

The large increase in I stability by bisulfite at acidic pH cannot be attributed to the effects of ionic strength but must be attributed to the protection of I by some direct interaction. To confirm that the peaks at 190 sec (FIGS. 1B and 1E) (pH 2.5 sample) were due to I and not to the bisulfite-I product (III), the u.v. spectra of all peaks at 190 sec (FIGS. 1A–1E) were recorded and found to be identical to those obtained from pure I. This finding demonstrates that whatever the stabilization mechanism, the addition product (III) eluted as I when the procedure of Example A was used and the Zorbax column with the mobile phase (0.02 M phosphate buffer; pH 6.5) at a flow rate of 2.0 ml/ml.

Figure 2:
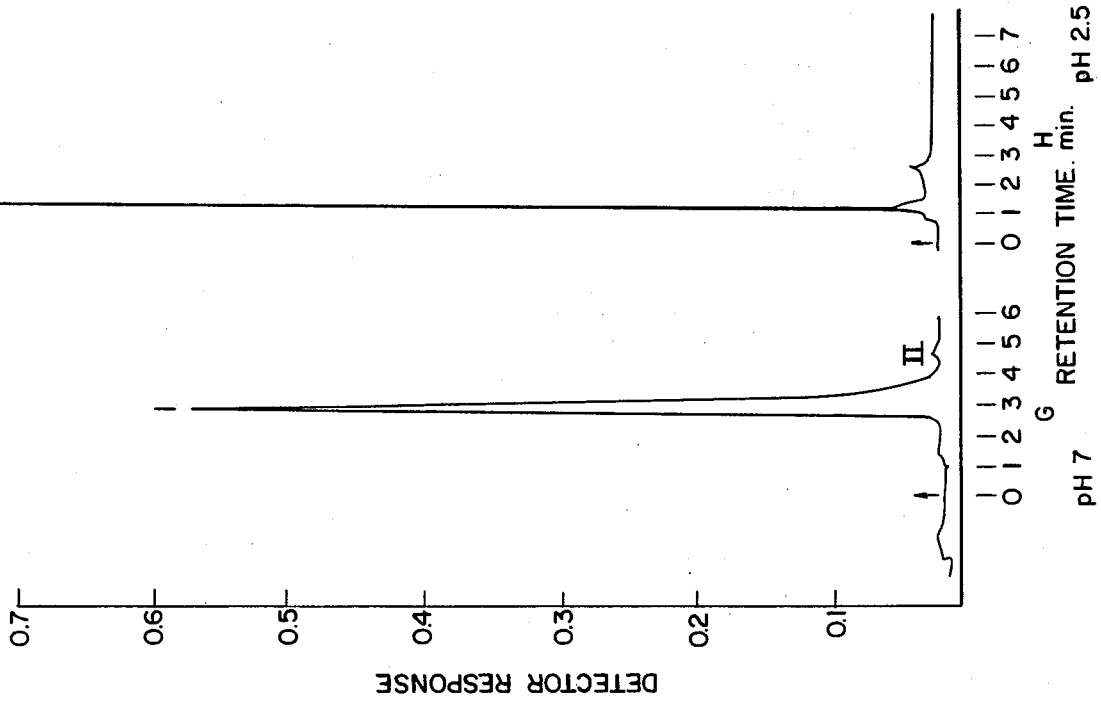
FIG. 2 is a graph of chromatograms obtained by another HPLC method in which the mobile phase has a pH of 2 of I with and without bisulfite.

In FIG. 2 chromatograms comparing Solution I alone and Solution I with bisulfite, eluted by HPLC having a mobile phase with a pH of 2 are given. Note that FIG. 2H shows the absence of peak I. The solution used was one obtained from the pH 2.5 sample represented in FIG. 1B. Therefore, III remained intact and did not elute as a peak corresponding to I. However, at pH 6.5, III rapidly reverted back to I; therefore, the peak resulting from III corresponds to I alone.

FIG. 3 shows the u.v. spectrum of I and III in 0.05 M phosphate buffer at different pH values. The concentration of I in the spectrophotometer cell was 30 micrograms/ml. Line A shows I at pH 2.5; Line O is III at pH 2.5; Line C is I at pH 6.5; and Line D is III at pH 6.5.

Another indication of the reversibility of III to I at pH 6.5 was obtained when equimolar (based on molar concentration of I) concentrations of I and the bisulfite-I mixture gave similar u.v. spectra (FIG. 3) at pH 6.5 (both I and the bisulfite-I mixture had $\lambda_{max}$ of 239 nm, $\epsilon = 6800$). However, at pH 2.5, the spectrum (FIG. 3) obtained from the bisulfite-I mixture was much less intense and different from that obtained with I (at pH 2.5, I had $\lambda_{max}$ at 241, $\epsilon = 3700$, and the bisulfite-I mixture had $\lambda_{max}$ at 243, $\epsilon = 1900$). Since the loss of absorption at 240 nm reflects the loss of the 5-6 double bond (8,9), it is reasonable to suggest that the lower value at pH 2.5 of the bisulfite-I mixture was due to addition of bisulfite across this bond.

It has thus been demonstrated that if the solution in I is maintained at pH 2.5 and if a five- to ten-fold excess of sodium bisulfite (relative to the concentration of I) is provided, I is stable, less than 10% degradation, for 20 hr. at room temperature and for about 4 days at refrigeration temperature. This conclusion represents a substantial improvement in the stability of I in solutions. Further, the ready reversibility of the bisulfite-I addition product (III) to yield I at neutral pH values indicates that III will quickly convert to I in the body and thus act as a I prodrug. Such increased stability will assure better control over the preparation of the I infusion solutions and over the dose being administered.

The results of this study also indicate that 1–2 g of sodium bisulfite would be necessary to provide a stable solution of 200 mg of I to be infused over 24 hr. Infusions of similar amounts of sodium bisulfite in commercial amino acid solution are used routinely, so it appears unlikely that addition of bisulfite would add significantly to the drug toxicity. The mixture of I with bisulfite also holds promise as an oral dosage form. The administration of I alone is not practicable because of its relatively short stability at 37° over the pH range of the stomach and intestine.

The following experimental procedures and examples illustrate the invention.

The 5-azacytidine (I) was obtained from Ben Venue Laboratories, Bedford, Ohio, Lot BV-77-270, and injected in 100 mg doses. Water was double distilled in an all-glass apparatus. All other chemicals are reagent grade.

A high pressure liquid chromatograph, Model 3500 B, available from Spectra-Physics, Santa Clara, Calif., equipped with a fixed volume loop type injection valve (Velco type also from Spectra-Physics) and a variable wavelength detector with a wavelength drive (Model SF 770 spectroflow monitor with SFA 339 wavelength drive, Schoeffel Instrument Corp., Westwood, N.J.) attached to a computing integrator (Autolab System I, from Spectra-Physics) were used. The columns used were a 250 mm by 4.6 mm inner diameter reversed-phase column designated Zorbax C-8 column, 6 micron average particle size from DuPont Instruments, Wilmington, Del., and a 250 mm by 3.2 mm inner diameter strong cation exchange column designated Partisil 10 SCX, 10 micron average particle size from Altex Scientific, Berkeley, Calif. Spectrophotometric analyses employed a recording spectrophotometer, Cary 17, from Varian Instrument Division, Palo Alto, Calif. All pH measurements were taken at room temperature on an Expandomatic SS-2 pH meter from Beckman Instruments, Fullterton, Calif.

EXAMPLE A

This example is illustrative of preparing a solution of I in pH 7.0 buffer.

A solution if I (0.5 mg/ml) was made by accurately weighing about 10 mg of I in a 20 ml screw-capped vial and adding 20.0 ml of pH 7.0 buffer which is 0.05 M phosphate. The freshly prepared solution was assayed by HPLC method 1. A reversed phase Zorbax column with the mobile phase (0.02 M phosphate buffer, pH 6.5) at a flow rate of 2.0 ml/min was used. A 10-microliter full loop sample volume was injected quantitatively, and the recorder was set at 0.64 full scale (254 mm detector). The area of the peak due to I was used to calculate the amount of intact I remaining in the sample. The run time was about 6 minutes. The u.v. spectrum of the peak was recorded for identification by stopping the flow at the maximum of the peak and scanning the peak from 300 to 200 nm using the wavelength drive of the detector. p The result of the assay is shown as A in FIG. 1. The small peak II, a major degration product, is the result of hydrolytic action as previously indicated in the above schemat.

EXAMPLE A-1

In this testing on mice there was a comparison made of the activity of two samples of 5-azacytidine. Sample RR included 5-azacytidine; Sample RS included 5-azacytidine bisulfite prodrug. This analysis for activity determined that there is no significant difference in activity between RR and RS samples although the ILS percent values are somewhat lower for the RS batches. In addition, the mice dying of toxicity (in those experiments prior to Day 9) have been removed from the Day 30 survivals and in this case a standard dosage at Days 1, 4 and 9 was utilized. In addition, it was noted from this that the RS sample was slightly more toxic when administered i.p. but this was not true of the i.v. and oral route.

EXAMPLE B

Solutions of I, as in Example A, with the exception with sodium bisulfite was included into the buffer before adjustment of its final pH. One solution with a pH of 7.0 (0.05 M phosphate) was prepared and another with a pH of 2.5 (0.05 M phosphate).

The procedure of Example A was followed and the results for both pH solutions (freshly prepared) is shown in FIG. 1, at B.

EXAMPLE C

The same solution of Example A was again assayed as before after a 70-minute retention period of the solution at room temperature. The results are shown in FIG. 1C. A loss of about 7% of I is accompanied by an increase in peak II, the degradation product.

EXAMPLE D

The solution of Example B at a pH 7 was reassayed by the procedure of Example A after a 70-minute wait at room temperature. The results are shown in FIG. 1D. The degradation loss was almost 15%.

EXAMPLE E

The solution of Example B at pH 2.5 was reassayed after 70 minutes at room temperature by the procedure of Example A and the results are shown in FIG. 1E. There was not discernable difference between FIG. 1B and 1E. This indicated that, surprisingly, bisulfite had a strong stabilizing effect on I hydrolysis at pH 2.5.

EXAMPLE F

A solution was prepared according to Example A except the pH was adjusted to 2.5 by 0.05 M phosphate. After a period of 70 minutes at room temperature, the solution was assayed. The results are shown in FIG. 1F. As can be seen, a major degradation product II was eluted indicating solution I alone was not stable at pH 2.5.

In order to demonstrate that an addition product of I-bisulfite, designated III, is responsible for the stabilization of I at pH values less than 4, solutions of III were prepared and assayed on a second column (Partisil 10 SCX) with a mobile phase of a pH of 2. The following examples illustrate this.

EXAMPLE G

A solution was prepared identical to the solution in Example A. A strong cation-exchange column (Partisil 10 SCX) was used. The mobile phase consisted of 0.01 M NaCl with 0.01 M HCl in water (pH 2) and was pumped at 1.25 ml/min. A 10-micron liter full loop sample volume was injected and the recorder was set at 0.32 full scale (254 nm detector). The result is shown in FIG. 2G. This established the graph for I under these HPLC conditions.

EXAMPLE H

The freshly prepared solution of Example B at pH 2.5 was assayed as in Example G. The result is shown in FIG. 2H. There is no peak corresponding to I. Therefore, in spite of high dilution during the HPLC procedure, when the mobile phase of low pH (pH 2) was used, III remained intact and did not elute as a peak corresponding to I. However, at pH 6.5, III rapidly reverted back to I; therefore, the peak resulting from III corresponds to I alone.

We claim:
1. In a method of administering 5-azacytidine internally in mice, the improvement comprising the steps of:
   (a) a stabilizing the 5-azacytidine by forming a pro-drug form which has a bisulfite addition compound across the 5-6 imine double bond at about a pH of 2.5, and
   (b) infusing the pro-drug of 5-azacytidine into the body wherein the physiological environment of the body at a pH >6 restores the pro-drug to the active 5-azacytidine form.
2. A method of claim 1 wherein 1-2 grams of sodium bisulfite are provided for a solution of 200 mg of 5-azacytidine to be infused in 24 hours.

* * * * *